United States Patent

Robert et al.

[11] Patent Number: 5,665,315
[45] Date of Patent: Sep. 9, 1997

[54] AUTOMATIC CONNECTION BOX FOR DISTRIBUTING REAGENTS IN A HAEMATOLOGICAL ANALYZER

[75] Inventors: Jean-Edouard Robert, Neuilly sur Seine; Roger Le Comte, Carnon; Henri Champseix, Montferrier S/Lez, all of France

[73] Assignee: ABX SA, Montpellier, France

[21] Appl. No.: 516,550

[22] Filed: Aug. 18, 1995

[30] Foreign Application Priority Data

Aug. 18, 1994 [FR] France .................. 94 10106

[51] Int. Cl.⁶ .............. B01L 3/00; B01L 11/00; G01N 33/48; G01N 27/30
[52] U.S. Cl. .............. 422/102; 422/63; 422/65; 422/81; 422/103; 204/401
[58] Field of Search ............... 422/61, 63, 65, 422/102, 103, 81; 206/221; 220/403, 404; 204/401, 403

[56] References Cited

U.S. PATENT DOCUMENTS

| | | | |
|---|---|---|---|
| 3,647,386 | 3/1972 | Gilford | 422/102 X |
| 3,647,397 | 3/1972 | Coleman | 422/102 X |
| 4,286,636 | 9/1981 | Credle | 141/114 |
| 4,353,488 | 10/1982 | Schneiter et al. | 222/501 |
| 4,375,864 | 3/1983 | Savage | 222/81 |
| 4,445,551 | 5/1984 | Bond et al. | 141/349 |
| 4,548,606 | 10/1985 | Larkin | 604/414 |
| 4,570,827 | 2/1986 | Roggenburg, Jr. et al. | 222/95 |
| 4,588,554 | 5/1986 | Kaartinen et al. | 422/61 |
| 4,871,439 | 10/1989 | Enzer et al. | 204/401 |
| 5,031,797 | 7/1991 | Boris et al. | 222/23 |
| 5,171,538 | 12/1992 | Tremmel et al. | 422/100 |
| 5,279,797 | 1/1994 | Burns et al. | 422/102 |
| 5,467,806 | 11/1995 | Stricklin et al. | 141/346 |

FOREIGN PATENT DOCUMENTS

| | | |
|---|---|---|
| 0192794 | 9/1986 | European Pat. Off. . |
| 0431352 | 6/1991 | European Pat. Off. . |

*Primary Examiner*—Arlen Soderquist
*Attorney, Agent, or Firm*—Birch, Stewart, Kolasch & Birch, LLP

[57] ABSTRACT

The analyzer (4) comprises a single box (1) for the distribution of reagents and which is removable from, and connectable to, the said analyzer, the said box containing a plurality of flexible, retractable bags filled with reagent and a flexible bag for collecting the residues. The box (1) is places on a horizontal supporting plate (5) which slides along the side of the apparatus and which is mounted on springs (6). Upwardly orientated fixed metallic needles (7) pass through orifices (9) in the said supporting plate.

6 Claims, 5 Drawing Sheets

AUTOMATIC CONNECTION BOX FOR DISTRIBUTING REAGENTS IN A HAEMATOLOGICAL ANALYZER

The invention relates to a haematological analyzer and, more particularly, to an automatic connection box for distributing reagents in the said analyzer.

BACKGROUND OF THE INVENTION

It is known that these apparatus cannot operate without making use of liquid reagents, which comprise, at least the following: an isotonic diluent, a lysing agent and a detergent. These products are traditionally packaged in bottles or containers and, in order to use them, they have to be drawn off from each container via hoses which are extended by rigid tubes so that they can reach the bottoms of the reservoirs. Air must also be able to enter each container. Analyzer start-up is thus subject to a number of delicate connection operations; furthermore, once it has been connected up, the analyzer, with its hoses and the said associated reservoirs, is more difficult to displace.

It is especially to overcome this drawback that the Applicant has devised a system for the compact storage and the distribution of reagents which is fitted to one side of the apparatus and automatically ensures connection of the product-containing reservoirs to the analyzer. Furthermore, the device in question causes the residues to be connected to a special container, without this involving any increase in the volume of the whole.

SUMMARY OF THE INVENTION

One main object of the invention is thus a box for the distribution of reagents in an apparatus, in particular a haematological analyzer, which contains at least a plurality of downwardly orientated flexible, retractable bags without air intakes, filled with reagent, the closure members of which are flush with the base of the said box, the said box being dimensioned so as to fit onto the side of an apparatus and to ensure the connection of the bags of reagent through the opening of their closure members.

The box also contains an upwardly orientated flexible, retractable bag for residues.

According to one advantageous feature of the invention, the reagent distribution box is located on a horizontal supporting plate which slides along the side of the apparatus, with upwardly orientated mechanisms for opening the closure members passing through orifices in the said supporting plate. The opening mechanisms are metallic needles for piercing perforatable bungs, or fixed elements coming to bear against a closure member serving as a check valve which closes a central shaft in the bung. In addition, a lug hinged on the top of the analyzer holds the reagent distributing box in place on the plate and can be used to house a supply pipe for the residue bag, the neck of which emerges at the upper part of the reagent distribution box.

BRIEF DESCRIPTION OF THE DRAWINGS

Further characteristics and advantages of the invention will emerge from the following description of a non-limitative example of an embodiment wherein reference is made to the annexed drawings, which represent.

DETAILED DESCRIPTION OF THE INVENTION

Figure 1:
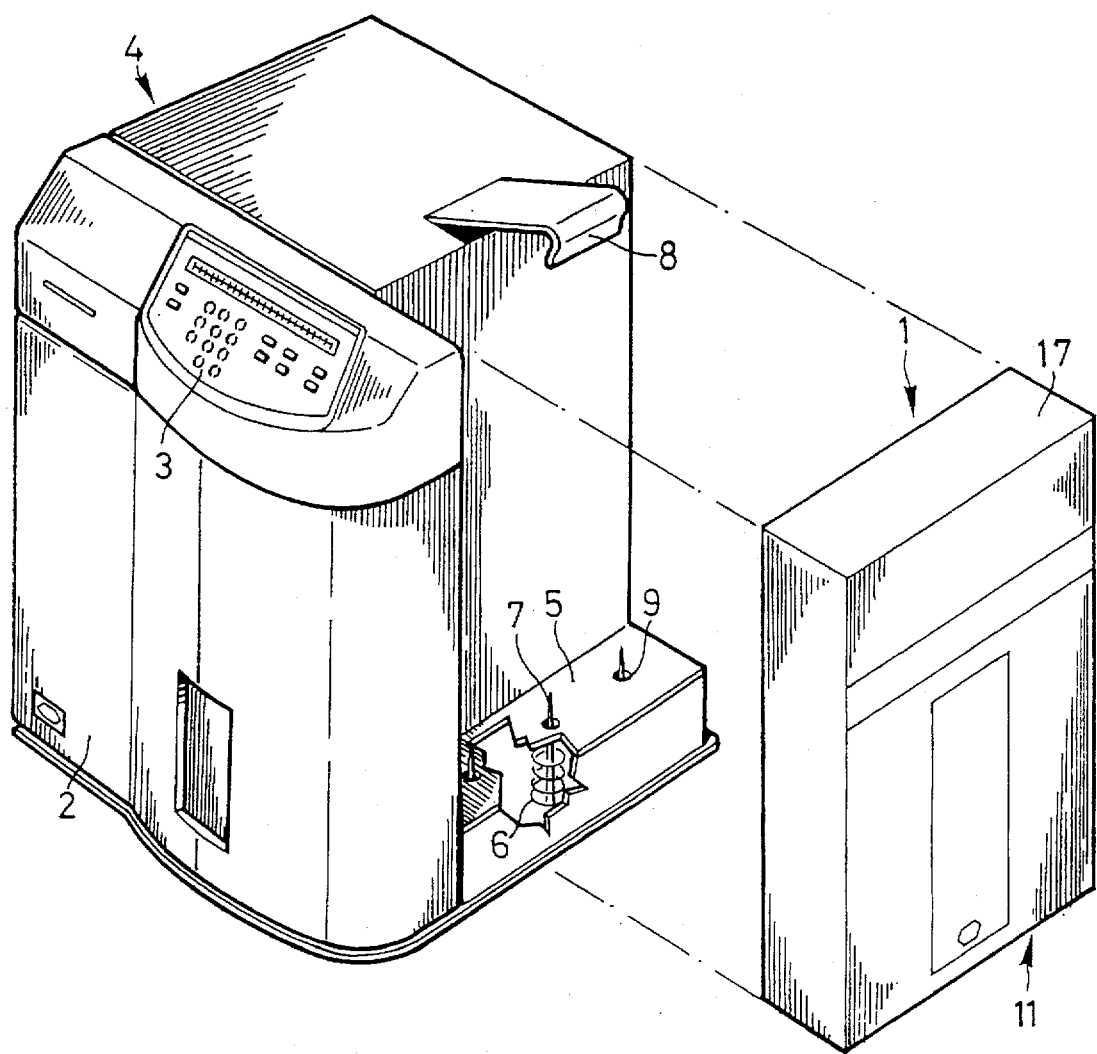
FIG. 1, an exploded perspective view, with parts stripped away, of the analyzer.
Figure 7:
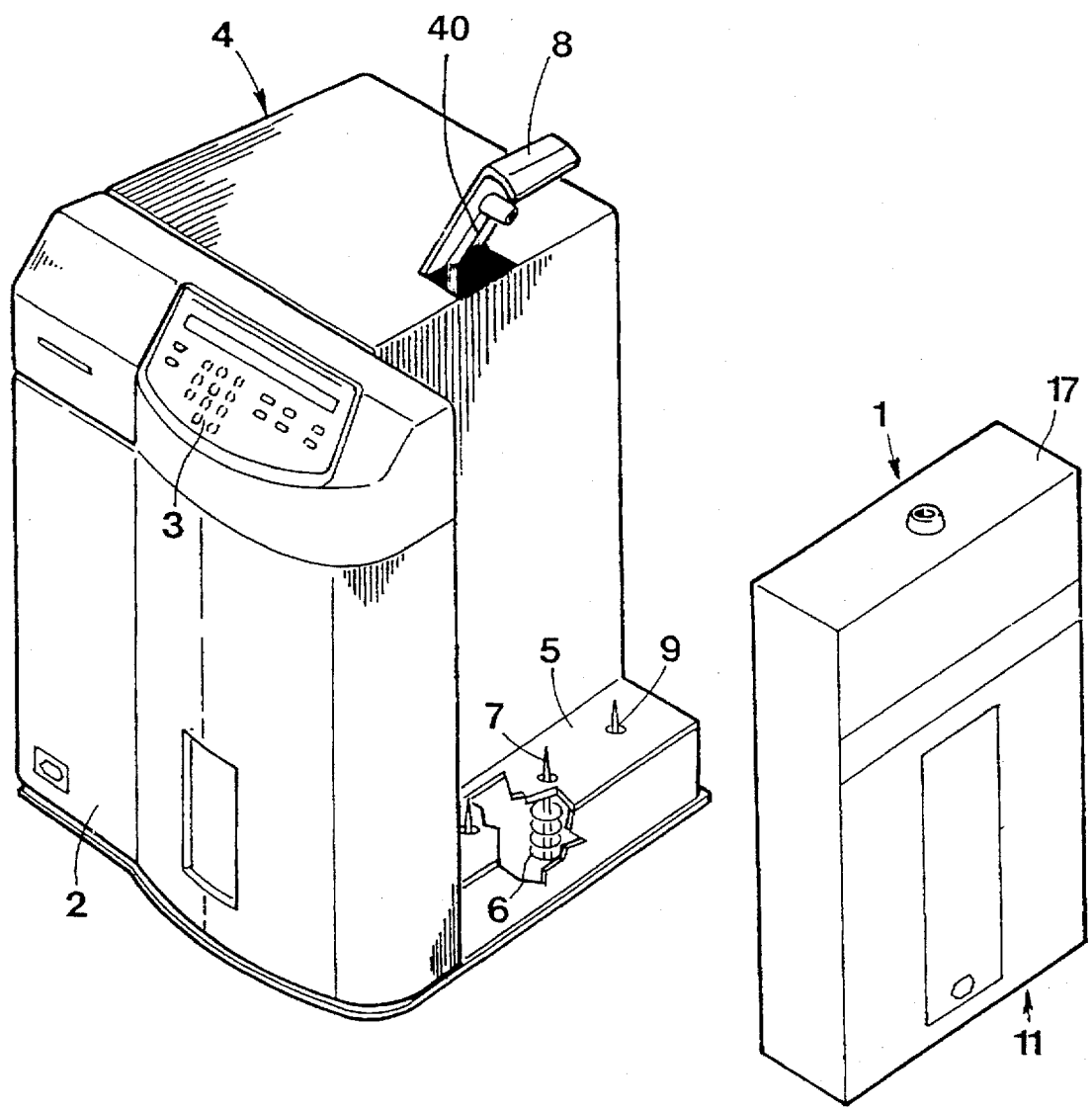

FIG. 1 shows a parallelepipedically shaped haematological analyzer 4, the front face 2 of which bears a control and display panel 3. The reagent distribution box, generally designated by reference number 1, is located on the side of the apparatus. It is removable and is dimensioned to fit thereon as an extension of its contours. It comes to bear on a horizontal supporting plate 5 slidingly mounted on springs 6, which maintain it in top position. Upwardly orientated fixed metallic needles 7 pass through small orifices 9 provided in the supporting plate. They are connected by tubes, not shown, to the measuring devices placed inside analyzer 4. On the upper portion, a lug 8 hinged on the top of the analyzer holds the box in place. According to an alternative form of embodiment, not shown, lug 8 can cover the entire width of the apparatus. Advantageously, it could be thicker so as to house a supply pipe 40 for a residue bag, to be discussed later (FIG. 7).

Figure 2:
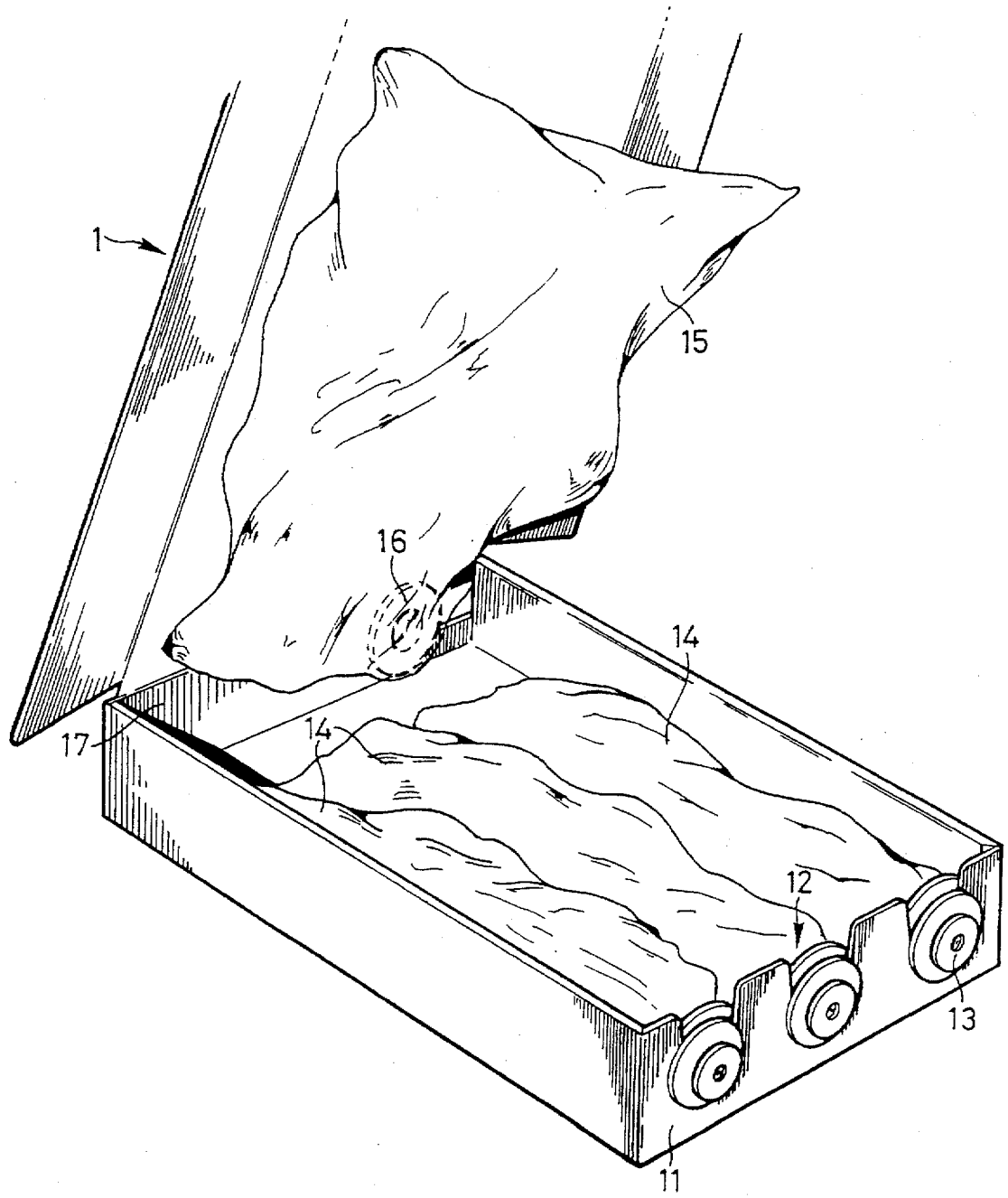
FIG. 2, a perspective view of the reagent distribution box in open position.

FIG. 2 shows a distribution box 1 taking the form, for example, of a recipient the lower portion 11 of which, designed to rest on plate 5, is provided, perpendicular to needles 7, with cut-out portions 12 in which are positioned perforatable bungs 13 made of silicone, each of which closes a corresponding flexible bag 14. Perforatable bungs 13 are thus flush with the base of the box. In the case in point, there are, inside the box, three flexible bags of different capacities, each containing a reagent. These bags 14 are of the type used, for example, for packaging wine and which are known to be capable of retracting as they empty. These bags 14 are thus disposed with their necks facing downwards in receptacle 1; they are shown empty in the figure. The said distribution box also contains another flexible bag 15, of slightly larger capacity, the neck 16 of which is orientated upwards and emerges at the level of a cut-out portion of the upper part 17 of the said box. This bag is designed to receive metering residues, possibly by means of a pipe housed inside the holding lug.

To operate the apparatus, the three flexible bags 14 are thus each filled with their reagent and they are positioned inside the same box 1, the volume/internal space of which they almost completely fill. On the other hand, flexible residue bag 15 is empty and compressed inside the receptacle by the bags of reagent.

Box 1, thus filled, is easily positioned on the side of analyzer 4, with its lower face 11 placed on plate 5. Through the effect of the weight of the box, and by exerting additional pressure, plate 5 is caused to descend, compressing springs 6 and, when this movement occurs, needles 7 automatically pierce bungs 13 of each bag 14. The corresponding reagents are thus connected to the analyzer. The liquids can thus be transferred to the machine. Once the box has finished travelling downwards on plate 5, the user can lock it against the analyzer by means of a lug 8.

In proportion as bags 14 empty, they contract and, simultaneously, residue bag 15 fills and swells via its supply pipe. The volume of all the products contained in box 1 thus remains constant.

When one has finished using the reagents, the box can be detached from the analyzer by adopting the reverse procedure.

For the user, manipulations are thus considerably simplified and take no more time than if there were only one reagent to connect up.

Figure 3:
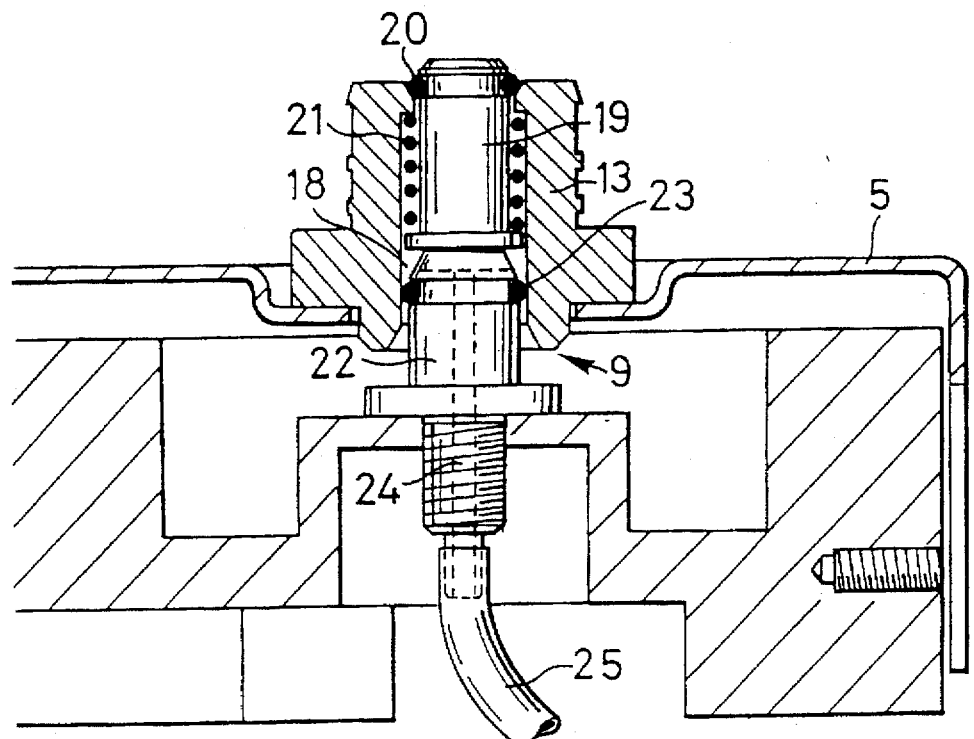
FIGS. 3 and 4, views of a closure member acting as a check valve for the bungs of the reagent bags, in closed and open positions respectively.
Figure 4:
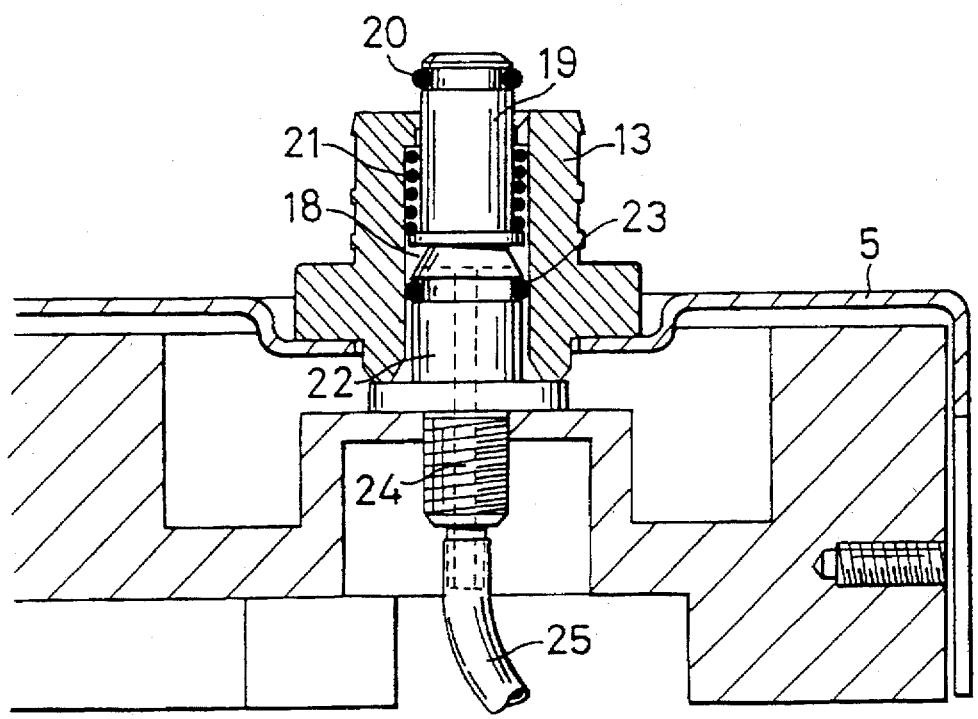

FIGS. 3 and 4 illustrate another form of embodiment of the invention permitting quick connection of the bags of the box without any need to use perforating needles. For this purpose, bung 13 is no longer a solid silicone bung but is pierced by a central shaft 18 inside which can travel a member 19 for closing the shaft in question, the head of this member being fitted with an O-ring 20 bearing on the profiled orifice of shaft 18. Closure member 19, acting as a check valve, is held in the closed position illustrated in FIG. 3 by means of a spring 21. The outer portion of bung 13 fits into the neck of a flexible bag of reagent.

The apparatus designed to receive the reagent box again has a mobile plate 5. However, each perforating needle is remplaced by a fixed element 22, fitted with a seal 23, which projects from an orifice 9 in plate 5. Through the element passes an internal conduit 24 connecting to a pipe 25 for supplying the apparatus with reagent. When the reagent box is positioned on plate 5, the end of element 22 penetrates central shaft 18 in bung 13 and comes into abutment against the base of closure member 19.

In proportion as supporting plate 5 moves down (FIG. 4), element 22 pushes closure member 19 against the bias of spring 21 and disengages seal 20 from shaft 18. The reagent can thus flow through the shaft, and thence into conduit 24 and pipe 25.

Figure 5:
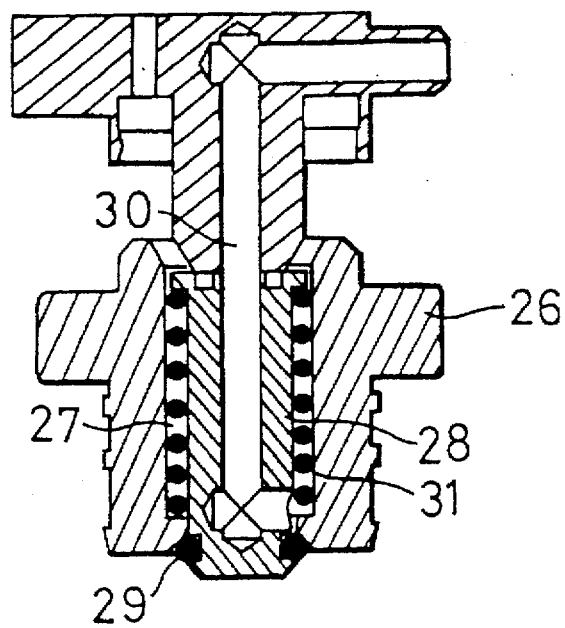
FIGS. 5 and 6, views of a closure member for the bung of a residue bag in closed and open positions respectively.
Figure 6:
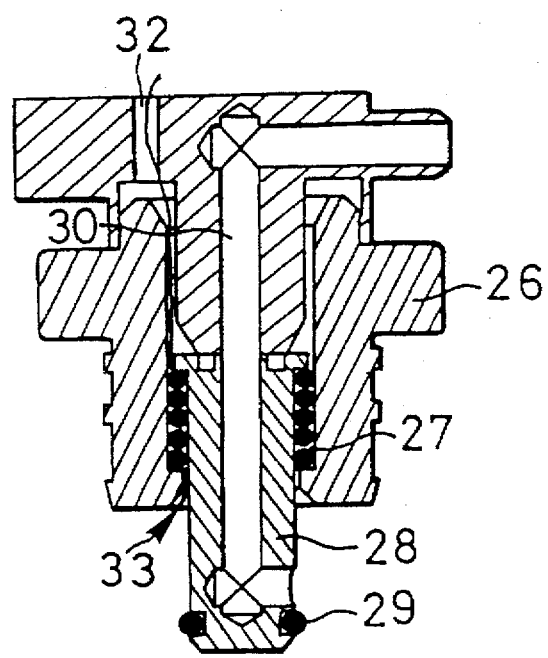

For the residue bag, use can be made of a closure member somewhat similar to that used for the bags of reagent, as seen in FIGS. 5 and 6. The residue bag is fitted with a bung 26 analogous to bung 13. Its central shaft 27 can be penetrated by a closure member 28 the end of which is fitted with a seal 29 and through which passes a central conduit 30 for residue transfer. A return spring 31 holds the said closure member in closed position (FIG. 5). When the apparatus is in operation, the residues are injected by pressure into conduit 30, the closure member 28 being driven into shaft 27 and clipped to bung 26. The residues then escape into the bag via the lower orifice in the conduit (FIG. 6). Air is admitted into the bag via an orifice 32 in the closure member which communicates with the central shaft and the interior of the bag via the annular space 33 between the bung and the closure member.

We claim:

1. A system for distributing reagents in an analytical instrument comprising:

an analyzer device and a reagent distribution device, said analyzer device including a horizontal supporting plate disposed at a side thereof, the horizontal supporting plate being moveable in a vertical direction and having a plurality of orifices therethrough, said analyzer device further including a plurality of upwardly oriented opening mechanisms located below said plurality of orifices, said reagent distribution device being dimensioned to fit onto the side of said analytical device and including a container structure having a first end and a second end, a plurality of flexible retractable reagent bags disposed within said container structure, and at least one retractable residue bag disposed within said container structure, wherein each of said plurality of reagent bags extends between said first and second ends and has a reagent closure member disposed at said first end of said container structure and each of the at least one residue bag extends between said first and second ends and has a residue closure member disposed at said second end of said container structure, such that, when said first end of said container is placed on the horizontal supporting plate, the supporting plate slides along the side of the analyzer device, and at least one of said opening mechanisms passes through said orifices and engages with a corresponding one of said reagent closure members.

2. The reagent distribution system according to claim 1, wherein the reagent closure member is a check valve having a central shaft therethrough with a check valve element disposed therein and said opening mechanism is a fixed element engageable against said check valve element for opening said central shaft.

3. The reagent distribution system according to claim 2, wherein said check valve element has a head about which is fitted an O-ring bearing on the profiled orifice of said central shaft.

4. The reagent distribution system according to claim 1, wherein said analyzer device further includes a lug structure hinged upon the top of the analyzer for holding said reagent distribution device on the plate, wherein the lug structure includes at least one pipe for supplying the at least one residue bag through said residue closure member.

5. The reagent distribution system according to claims 1 or 4, wherein said residue closure member has a central shaft therethrough and a moveable closure element disposed therein, said closure element having a central conduit therethrough for the transfer of residues.

6. The reagent distribution system according to claim 1, wherein said container structure has a predetermined internal volume in which said plurality of reagent bags and the at least one residue bag are disposed, at least one of said plurality of reagent bags containing fluid to be drained therefrom its said reagent closure member for transfer to said analyzer device, and at least one of the at least one residue bag receiving fluid through its said residue closure member from said analyzer device such that, upon transfer and receipt of the fluid, said at least one of said plurality of reagent bags contracts and said at least one of the at least one residue bag expands simultaneously.

\* \* \* \* \*